US012653516B2

(12) United States Patent
Jacob

(10) Patent No.: US 12,653,516 B2
(45) Date of Patent: Jun. 16, 2026

(54) LUNG TRANSPLANT RETRACTOR SYSTEM

(71) Applicant: Samuel Jacob, Jacksonville, FL (US)

(72) Inventor: Samuel Jacob, Jacksonville, FL (US)

( * ) Notice: Subject to any disclaimer, the term of this patent is extended or adjusted under 35 U.S.C. 154(b) by 0 days.

(21) Appl. No.: 18/802,276

(22) Filed: Aug. 13, 2024

(65) Prior Publication Data

US 2026/0047837 A1     Feb. 19, 2026

(51) Int. Cl.
*A61B 17/02*        (2006.01)
*A61B 17/00*        (2006.01)

(52) U.S. Cl.
CPC .... *A61B 17/02* (2013.01); *A61B 2017/00367* (2013.01); *A61B 2017/00477* (2013.01); *A61B 2017/00809* (2013.01); *A61B 2017/00836* (2013.01); *A61B 2017/00946* (2013.01)

(58) Field of Classification Search
None
See application file for complete search history.

(56) References Cited

U.S. PATENT DOCUMENTS

| | | | | |
|---|---|---|---|---|
| 4,726,356 A | * | 2/1988 | Santilli | A61B 17/0206 |
| | | | | 600/234 |
| 4,829,985 A | | 5/1989 | Couetil | |
| 5,167,223 A | * | 12/1992 | Koros | A61B 17/0206 |
| | | | | 600/234 |
| 5,365,921 A | * | 11/1994 | Bookwalter | A61B 17/0206 |
| | | | | 403/150 |
| 5,772,583 A | | 6/1998 | Wright et al. | |
| 5,951,466 A | | 9/1999 | Segermark et al. | |

| | | | | |
|---|---|---|---|---|
| 5,984,867 A | | 11/1999 | Deckman et al. | |
| 6,099,468 A | * | 8/2000 | Santilli | A61B 17/0206 |
| | | | | 600/232 |
| 6,102,854 A | | 8/2000 | Cartier et al. | |
| 6,290,644 B1 | * | 9/2001 | Green, II | A61B 17/0218 |
| | | | | 600/209 |
| 6,364,833 B1 | * | 4/2002 | Valerio | A61B 90/50 |
| | | | | 600/231 |
| 6,599,240 B2 | | 7/2003 | Puchovsky et al. | |
| 6,730,022 B2 | | 5/2004 | Martin et al. | |
| 6,837,851 B1 | | 1/2005 | Valentini et al. | |
| 6,896,654 B2 | | 5/2005 | Paolitto et al. | |
| 7,220,228 B2 | | 5/2007 | Hu et al. | |

(Continued)

FOREIGN PATENT DOCUMENTS

| | | | | |
|---|---|---|---|---|
| DE | 19844251 A1 | * | 4/2000 | ......... A61B 17/0206 |
| WO | WO-0180725 A1 | * | 11/2001 | ......... A61B 17/0206 |

OTHER PUBLICATIONS

English language translation of DE19844251A1 (Year: 2000).*

*Primary Examiner* — Eduardo C Robert
*Assistant Examiner* — Anna V. Little
(74) *Attorney, Agent, or Firm* — Dunlap Bennett & Ludwig PLLC; Anna L. Kinney

(57)        ABSTRACT

A surgical retractor device includes at least two retractor blades slidably attached by a tooth and gear mechanism, the blades having concave surfaces facing away from one another. The first concave retractor blade can be joined to a first end of a first bar that has a serrated edge The second concave retractor blade can be joined to a first end of a bar arm that has the gear mechanism at its opposite end. The gear mechanism includes a handle with a gear which causes the first bar to slidably move along the second bar. Each bar can include a housing with a fastener that can receive stabilizers.

9 Claims, 4 Drawing Sheets

(56)               References Cited

U.S. PATENT DOCUMENTS

|  |  |  |  |  |
|---|---|---|---|---|
| 7,507,202 | B2 | 3/2009 | Schoellhorn | |
| 7,736,308 | B2 | 6/2010 | Cohn et al. | |
| 7,824,332 | B2 | 11/2010 | Fakhrai | |
| 8,945,003 | B2 | 2/2015 | Bass et al. | |
| 9,049,989 | B2 | 6/2015 | Crenshaw et al. | |
| 10,092,282 | B2 | 10/2018 | Puskas et al. | |
| 11,452,514 | B2 | 9/2022 | Truckey et al. | |
| 2006/0100487 | A1* | 5/2006 | Cartier ............... | A61B 17/0206 600/232 |
| 2010/0185060 | A1* | 7/2010 | Farley ................ | A61B 17/0206 600/228 |
| 2015/0209022 | A1* | 7/2015 | Ruppert ............. | A61B 17/0206 600/219 |
| 2015/0327847 | A1* | 11/2015 | Fehling .............. | A61B 17/0206 600/215 |
| 2016/0000419 | A1* | 1/2016 | Weisshaupt ........ | A61B 17/0206 600/225 |

\* cited by examiner

LUNG TRANSPLANT RETRACTOR SYSTEM

BACKGROUND OF THE INVENTION

The present invention relates to cardio-thoracic surgical devices, and, more particularly, to a lung transplant retractor system adapted to provide vertical retraction to a chest wall and maximum exposure to the proximal hilum.

Clamshell thoracotomy is widely used for double lung transplantation. A critical aspect of lung transplantation is the anastomosis of the anatomical structures of the donor lung to the anatomical structure of the recipient, such as the blood vessels of the heart and the airway. Exposure of the hilum is critical to successful anastomosis but is also very challenging. Traditionally, at least two surgical assistants using bulky handheld retractors are needed to provide the necessary vertical retraction to the chest wall to effectively expose the proximal hilum of the lung. Extra surgical assistants can be subject to fatigue and also crowd the surgical field, which can lead to longer surgical times, high anastomosis revisions, and generally less desirable surgical outcomes.

As can be seen, there is a need for a surgical retraction device adapted to provide maximum vertical retraction to the chest wall and maximum exposure to the proximal hilum for a lung transplantation.

SUMMARY OF THE INVENTION

In one aspect of the present invention, a surgical retractor comprises a rack and pinion assembly including a rack bar having a first longitudinal axis, a slide end, a first blade end, and a longitudinal edge therebetween with teeth formed therein; a first arcuate retractor blade disposed at the first blade end, the first arcuate retractor blade having a first concave surface facing away from the rack bar; and a drive bar having a second longitudinal axis parallel to the first longitudinal axis, wherein the drive bar is longitudinally displaceably coupled to the rack bar, the drive bar having a drive end and a second blade end, with a second arcuate retractor blade disposed at the second blade end, the second arcuate retractor blade having a second concave surface facing opposite and away from the first concave surface; a rack-and-pinion drive fixedly mounted at the drive end, the rack-and-pinion drive having a slot formed therein, wherein the slot slidably accommodates the slide end of the rack bar in a position overlapping the drive bar; and a drive handle mounted to the rack-and-pinion drive, wherein the drive handle is operative to actuate the rack-and-pinion drive to travel longitudinally along the teeth.

In some aspects of the present invention, the surgical retractor has adjustably fastened thereto at least one tissue stabilizer, comprising a rod having a first end and a second end; and a stabilizer blade disposed at the first end.

Advantageously, the novel surgical device can be utilized for bilateral anterolateral thoracotomies, or clamshell thoracotomies, widely used in lung transplantation, and can provide maximum vertical retraction to the chest wall and maximum exposure to the proximal hilum without the need for additional surgical assistants.

These and other features, aspects and advantages of the present invention will become better understood with reference to the following drawings, description, and claims.

DETAILED DESCRIPTION OF THE INVENTION

Figure 1:
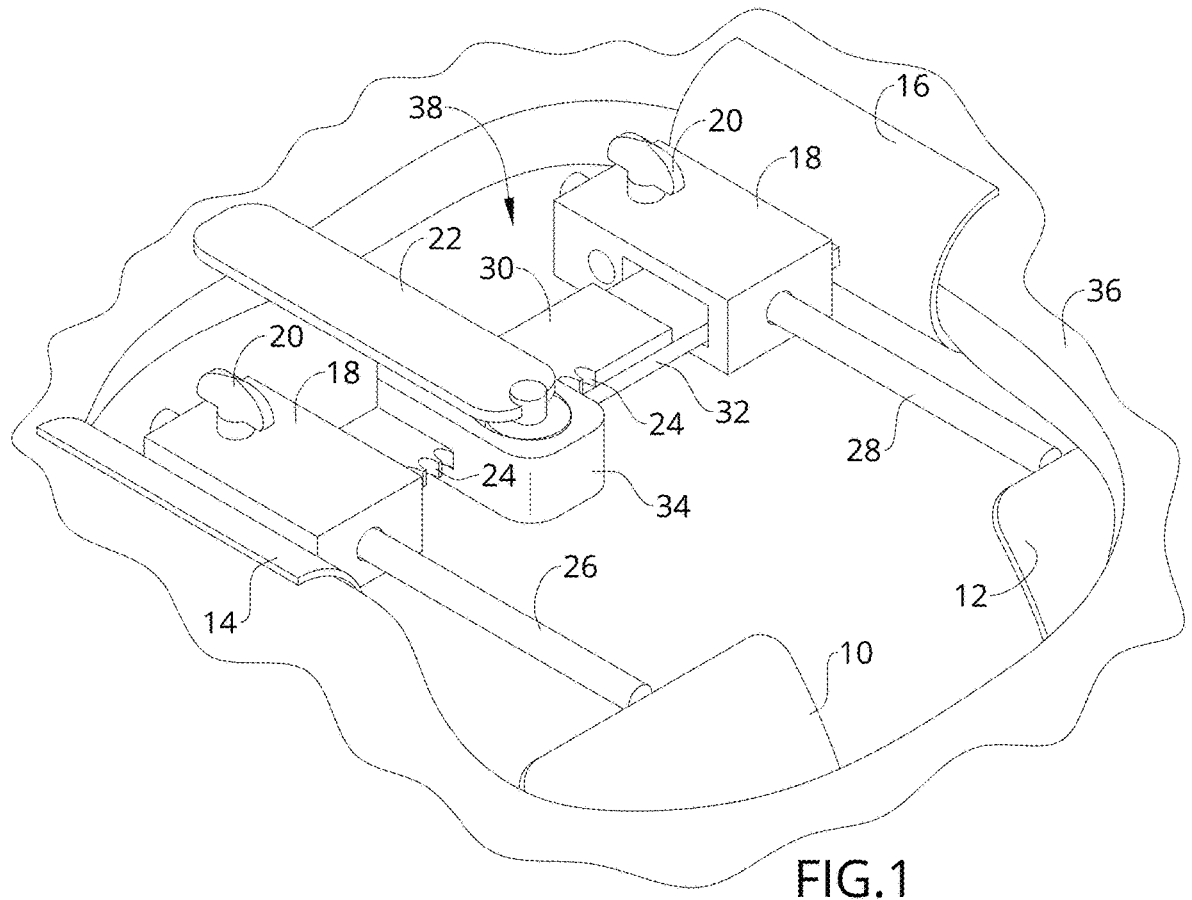
FIG. 1 is a perspective view of a surgical retraction device according to an embodiment of the present invention, shown in use.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a surgical retraction device adapted for use in thoracotomies used during lung transplantation. The device may spread the chest by any suitable dimension, such as up to about 8 inches.

The surgical retractor may have concave blades, which may have any suitable dimensions, such as about 2 inches wide by about 2 inches deep. Each blade is fused to a rod or arm, which may have a length of about 5 inches, for example.

The retractor may have two slidably coupled, overlapping arms—a toothed arm and a sliding and locking system arm.

A thoracic retractor or "rib spreader", such as the Finochietto-style retractor, is well known for use in lung transplantation. The prior art retractor is a mechanical device utilizing two opposed retraction elements or parallel arms. Each retraction element has a blade that is inserted into an incision, each blade engaging one side of the incision. One retraction element is moveable with respect to the other retraction element, with motion being driven by a ratchet or rack-and-pinion gear system that is manually driven with a drive handle. The retraction elements exert a force on the anatomical elements on either side of the incision to separate the anatomical elements, thereby opening the incision. A lock screw may be used to secure the position of the driven anchor block after adjustment. See, for example, U.S. Pat. No. 4,627,421 to Symbas et al. and U.S. Pat. No. 4,852,552 to Chaux.

The surgical retraction device can include at least two concave retractor blades, with each blade being disposed at an end of a bar. The rack bar may have ratchet teeth. The retractor blades can be slidably affixed to each other with a tooth and gear configuration, where a first bar can include the tooth grooves, and a second bar can have the gearing mechanism with an aperture configured to receive the first bar. Advantageously, the tooth and gear mechanism can allow customizable retraction and extension of the retractor blades for optimal exposure of the surgical site such that spacing between the blades can be adjusted while being maintained in a substantially parallel relationship to each other.

An additional aspect of the present invention can include at least one soft tissue stabilizer that can be removably affixed to the arms of the surgical device. The soft tissue stabilizer can include a curved blade for stabilizing soft tissue, and a rod connected to a portion of the curved blade. Advantageously, a surgical stabilizer can be added and/or removed, as needed, to support soft tissue, or other anatomical features of the surgical site, to provide better visualization and maneuvering at the surgical site.

The soft tissue stabilizer can be removably affixed to one of the arms of the surgical device by means of a fastener that includes a plurality of apertures. A first aperture of the plurality of apertures can be configured to receive an arm of the surgical device for slidable movement of the fastener. A second aperture can be configured to receive the rod of a soft tissue stabilizer for slidable placement of the stabilizer. Finally, a third aperture can be a threaded aperture configured to receive a threaded fastener for securing the rod of the stabilizer to the arm of the surgical device.

In embodiments, all components of the inventive surgical device can be made from medical grade surgical material, such as carbon steel, stainless steel, aluminum, or titanium, and are adapted to be easily sterilizable. In other embodiments, the system may be manufactured of disposable, single use material such as certain plastics.

Referring to FIGS. 1-4, an embodiment of a surgical retraction device is illustrated. FIG. 1 illustrates the inventive surgical device in use during a thoracotomy, situated in the chest cavity 38 of a patient 36. A first retractor blade 14 disposed on an arm or rack bar 30 with teeth 24 can be communicatively coupled to a second retractor blade 16 disposed on an arm 32 with a gearing mechanism 34 attached thereto. Gearing mechanism 34 can include a gear disposed on the interior, which can be actuated by manipulation of handle 22. In embodiments, handle 22 can be ratcheted to move the gear along the teeth 24 to retract or extend the surgical device. A first soft tissue stabilizer 10 disposed on one end of a rod 26 can be attached to the surgical device by insertion into stabilizer fastener 18 and secured by tightening of fastener 20. Similarly, a second stabilizer 12 disposed on one end of a rod 28 can be attached to the surgical device by insertion into stabilizer fastener 18 and secured by tightening of fastener 20. In embodiments, the combination of stabilizer fastener 18 and fastener 20 can act as a clamp, securing either, or both, of rods 26 and 28 to an interior wall of stabilizer fastener 18 through pressure exerted by the tightening of fastener 20. Advantageously, stabilizers 10 and 12 can provide support for soft tissue during a surgical operation, thereby providing enhanced visualization of the site and better maneuvering of surgical tools.

Figure 2:
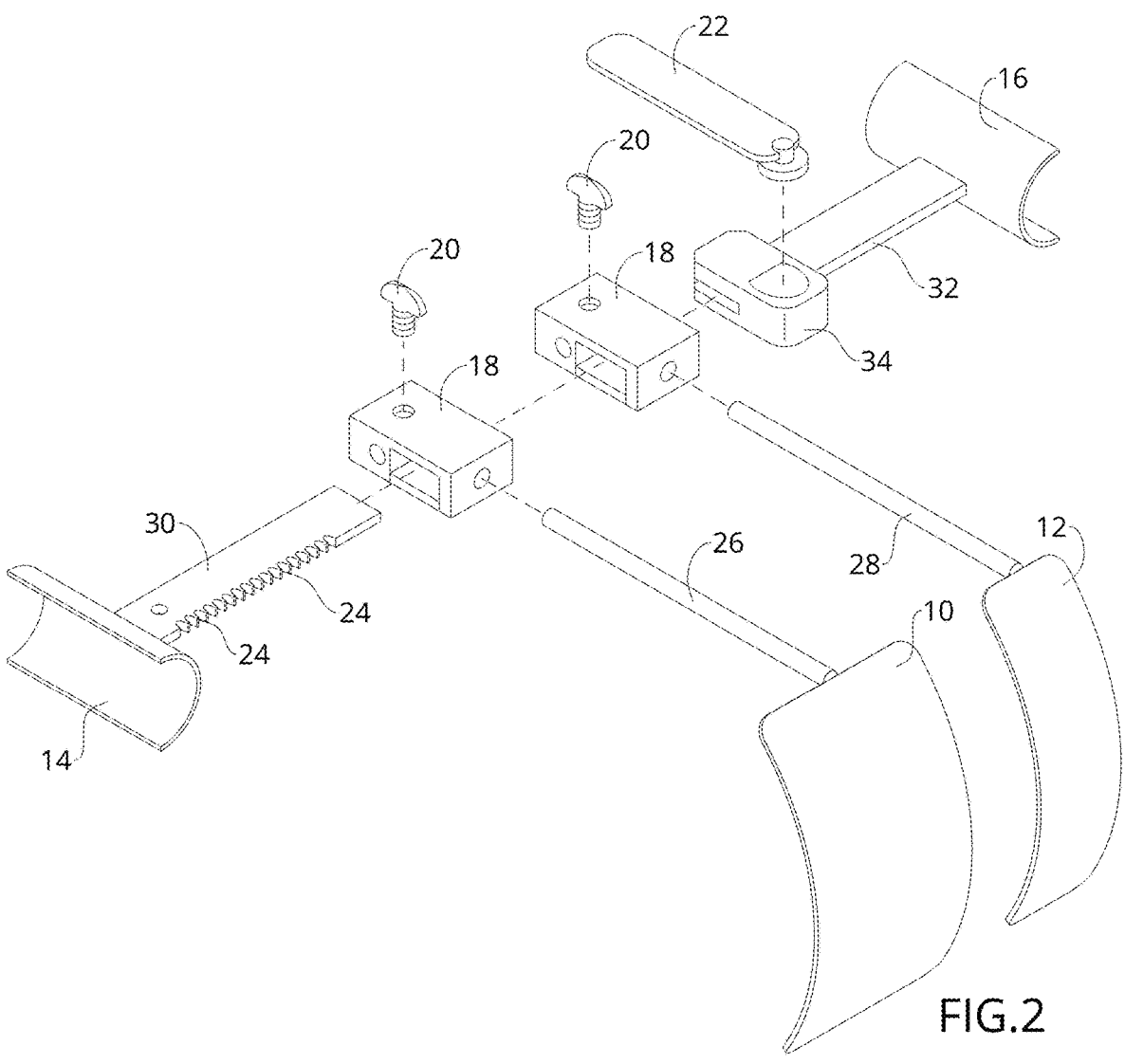
FIG. 2 is an exploded view thereof.

FIG. 2 illustrates an exploded view of a surgical retraction device. A first retractor blade 14 can be affixed to a first end of the rack bar 30, which can include teeth 24 usable in a tooth and gear system. The rack bar 30 can be adapted to receive a stabilizer fastener 18 with fastener 20, which can be adapted to secure additional peripheral devices to the surgical device. In embodiments, an additional peripheral device can include a stabilizer 10 affixed to a first end of a rod 26, which is adapted to be inserted into an opening in stabilizer fastener 18. A second retractor blade 16 can be affixed to a first end of an arm 32, which can have a gear housing 34 disposed at a second end. Gear housing 34 can include a gear usable in a tooth and gear system. Handle 22 can be attached to the gear and can be manipulated to move the gear along teeth 24 to retract, or extend, the surgical device as needed. In embodiments, the rack bar 30 can be inserted into gear housing 34 and can slidably move upon actuation of handle 22. In embodiments, an additional peripheral device can include a stabilizer 12 affixed to a first end of a rod 28, which is adapted to be inserted into an opening in stabilizer fastener 18. Advantageously, the surgical device can extend to provide maximum visualization of the surgical site, while reducing the amount of personnel necessary to provide said visualization.

Figure 3:
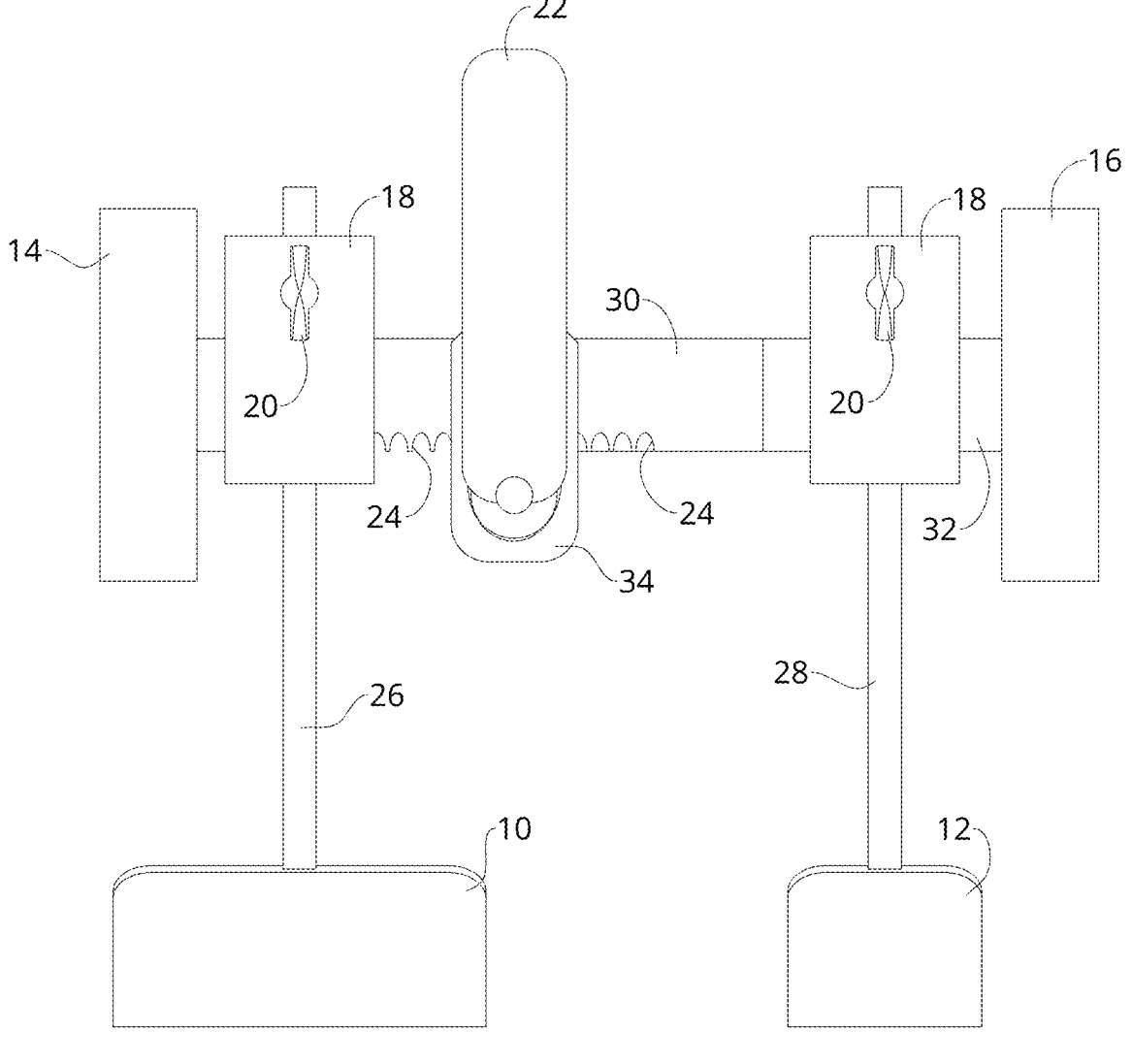
FIG. 3 is a top plan view thereof.
Figure 4:
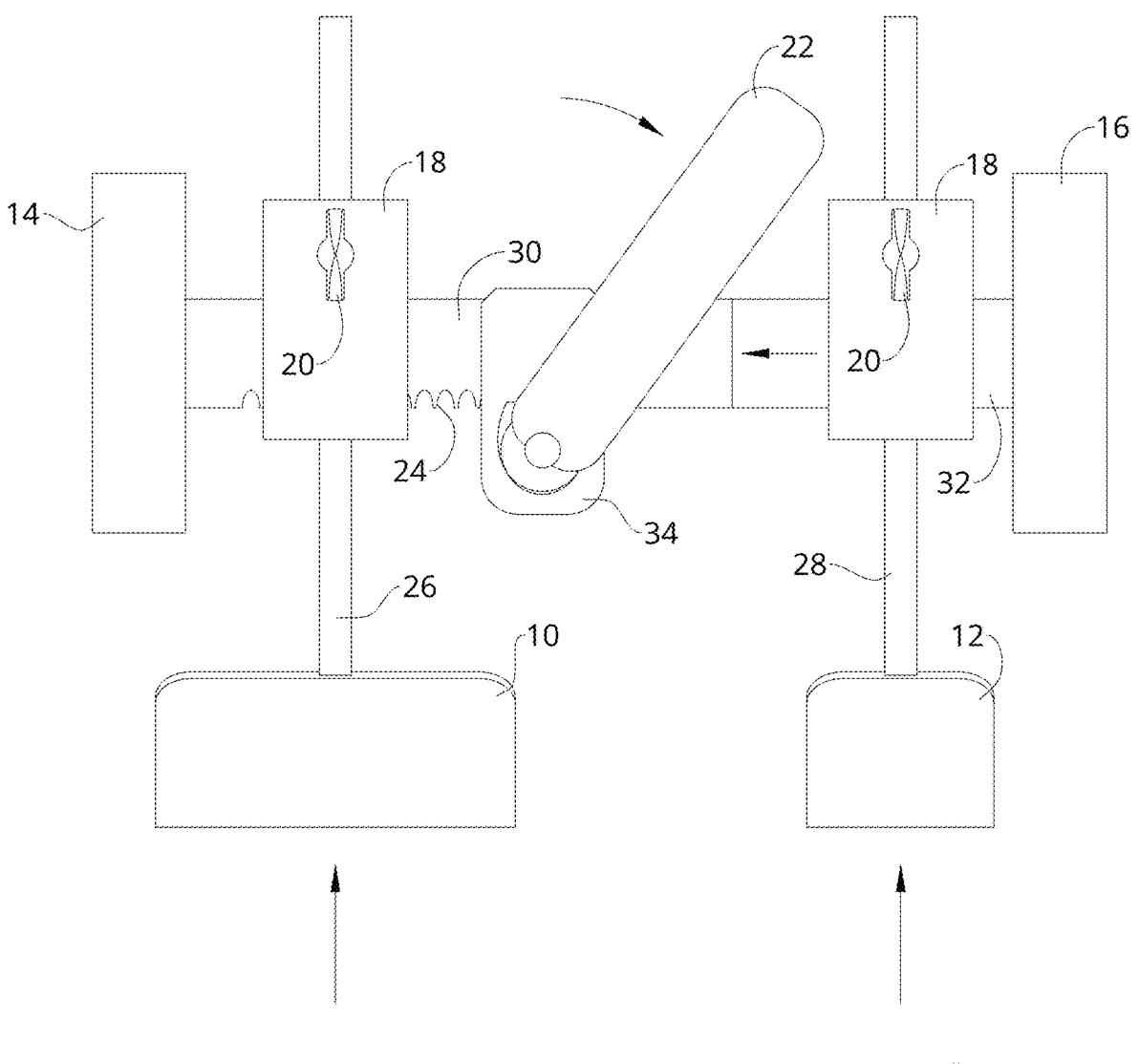
FIG. 4 is another top plan view thereof, shown in an alternate position.

FIGS. 3-4 illustrate a top view of the inventive surgical device and movement thereof. Actuation of handle 22 by a user can allow a gear disposed inside of gear housing 34 to move across teeth 24, thereby allowing the device to retract or expand in a lateral aspect dependent on the direction of actuation of handle 22. In embodiments, the rack bar 30 and 32 have a degree of overlap that reduces during expansion of the device and increases during retraction of the device. Additionally, stabilizers 10 and 12 can be set at customizable lengths by inserting more or less rods 26, 28 respectively into housing 18, and tightening fastener 20 when the desired position is reached. Advantageously, fastener(s) 20 can be loosened/tightened by hand, and can be adjustable during a surgical operation, as needed.

It should be understood, of course, that the foregoing relates to exemplary embodiments of the invention and that modifications may be made without departing from the spirit and scope of the invention as set forth in the following claims.

What is claimed is:

1. A surgical retractor, comprising:
a rack and pinion assembly including
    a rack bar having a first longitudinal axis, a slide end, a first blade end, and a longitudinal edge therebetween with teeth formed therein; a first arcuate retractor blade directly fused to the first blade end, the first arcuate retractor blade having a first concave surface facing away from the rack bar; and
    a drive bar having a second longitudinal axis parallel to the first longitudinal axis, wherein the drive bar is longitudinally displaceably coupled to the rack bar, the drive bar having a drive end and a second blade end, with a second arcuate retractor blade directly fused to the second blade end, the second arcuate retractor blade having a second concave surface facing opposite and away from the first concave surface;
    a rack-and-pinion drive fixedly mounted at the drive end, the rack-and-pinion drive having a slot formed therethrough, wherein the slot slidably accommodates the slide end of the rack bar in a position overlapping the drive bar; and
    a drive handle mounted to the rack-and-pinion drive, wherein the drive handle is operative to actuate the rack-and-pinion drive to travel longitudinally along the teeth.

2. The surgical retractor of claim 1, wherein the drive handle is pivotally mounted within the rack-and-pinion drive.

3. The surgical retractor of claim 1, wherein the rack and pinion assembly is formed of a metal selected from the group consisting of: carbon steel, stainless steel, aluminum, titanium, and any combination thereof.

4. The surgical retractor of claim 1, further comprising a fastener slidably coupled to the rack and pinion assembly, the fastener having:
    a fastener slot formed therethrough operative to accommodate the rack bar or the drive bar;
    a first bore formed therethrough, the first bore having a third longitudinal axis perpendicular to the first longitudinal axis and the second longitudinal axis;
    a threaded bore formed therein, the threaded bore having a fourth longitudinal axis perpendicular to the first longitudinal axis, the second longitudinal axis, and the third longitudinal axis; and
    a screw threadedly fastened within the threaded bore, wherein the screw is adjustably fastenable.

5. The surgical retractor of claim 4, wherein the screw is a thumbscrew.

6. The surgical retractor of claim 4, further comprising:

at least one tissue stabilizer, comprising:

a rod having a first end and a second end; and a stabilizer blade disposed at the first end;

wherein the first bore is operative to securely accommodate the rod.

7. The surgical retractor of claim 6, wherein the stabilizer blade has a convex surface facing away from the rack and pinion assembly.

8. The surgical retractor of claim 6, wherein the first bore is a through-hole through which the rod is adjustably coupled.

9. The surgical retractor of claim 6, further comprising a second tissue stabilizer having a second rod and a second stabilizer blade.

\*　　\*　　\*　　\*　　\*